(12) United States Patent
Ogawa

(10) Patent No.: US 11,116,473 B2
(45) Date of Patent: Sep. 14, 2021

(54) STETHOSCOPE

(71) Applicant: AMI INC., Minamata (JP)

(72) Inventor: Shinpei Ogawa, Kyoto (JP)

(73) Assignee: AMI INC., Kumamoto (JP)

( * ) Notice: Subject to any disclaimer, the term of this patent is extended or adjusted under 35 U.S.C. 154(b) by 211 days.

(21) Appl. No.: 16/086,008

(22) PCT Filed: Mar. 15, 2017

(86) PCT No.: PCT/JP2017/010506
§ 371 (c)(1),
(2) Date: Sep. 18, 2018

(87) PCT Pub. No.: WO2017/159752
PCT Pub. Date: Sep. 21, 2017

(65) Prior Publication Data
US 2020/0289083 A1 Sep. 17, 2020

(30) Foreign Application Priority Data

Mar. 18, 2016 (JP) .............................. JP2016-055893
Dec. 14, 2016 (JP) .............................. JP2016-242407

(51) Int. Cl.
*A61B 7/04* (2006.01)
*A61B 5/0408* (2006.01)
(Continued)

(52) U.S. Cl.
CPC ................ *A61B 7/04* (2013.01); *A61B 5/282* (2021.01); *A61B 5/6843* (2013.01); *A61B 2562/066* (2013.01)

(58) Field of Classification Search
CPC ............ A61B 7/04; A61B 5/0006; A61B 7/02
See application file for complete search history.

(56) References Cited

FOREIGN PATENT DOCUMENTS

EP    1943952 A1 * 7/2008 ............... A61B 7/04
JP    2015-20030 A    2/2015
(Continued)

OTHER PUBLICATIONS

International Search Report of International Patent Application No. PCT/JP2017/010506 completed Jun. 7, 2017 and dated Jun. 20, 2017 (3 pages).

(Continued)

*Primary Examiner* — Jon Eric C Morales
(74) *Attorney, Agent, or Firm* — Pyprus Pte Ltd; George D. Liu

(57) ABSTRACT

The present invention addresses the problem of providing a stethoscope having a structure which enables even physicians working remotely to recognize whether the chest piece of the stethoscope is touching the surface of the body appropriately. A stethoscope provided with: a stethoscope portion (10) comprising a chest piece and a microphone provided within the chest piece or in a hollow tube connecting to the chest piece; and sensors (20*a*-20*c*) for detecting contact with a human body, wherein the sensors detect contact by abutting with the body, and are fixed to the chest piece such that, when in a state detecting contact, the abutting ends of the sensors are situated in the same position as the contact surface of the chest piece against the body or in a position that is separated slightly farther from the body than the contact surface.

7 Claims, 6 Drawing Sheets

(51) Int. Cl.
*A61B 5/00* (2006.01)
*A61B 5/282* (2021.01)

(56) References Cited

FOREIGN PATENT DOCUMENTS

JP  WO2015170772 A1  11/2015
JP  WO2016143116 A1  9/2016

OTHER PUBLICATIONS

Written Opinion of International Patent Application No. PCT/JP2017/010506 completed Jun. 7, 2017 and dated Jun. 20, 2017 (6 pages).

* cited by examiner (a)

(b)

(a)

(b)

(a)

(b)

STETHOSCOPE

TECHNICAL FIELD

The present invention relates to a stethoscope having a chestpiece enabling a third person and a person placing the chestpiece on him/herself to recognize secured contact of the chestpiece with the body.

BACKGROUND ART

In telemedicine and telecare using a videophone or the like, when diagnosis is performed using a stethoscope, a stethoscope including a chestpiece having a built-in microphone is placed on a patient's body by the patient him/herself, converts heart sound or the like into an electric signal using the microphone, and transmits the electric signal to a remote doctor via communication.

SUMMARY OF INVENTION

Technical Problem

However, some patients are not used to using stethoscopes and chestpieces thereof are sometimes not in proper contact with patients' body surfaces. In such a case, in a conventional stethoscope, it is very difficult for a doctor to determine whether a chestpiece is properly in contact with a body by looking at visual information of a remote image. Improper contact of the chestpiece with the body surface may lead to misdiagnosis.

In view of the above description, it is an object of the present invention to provide a stethoscope having such a structure that a remote doctor or the like can recognize that a chestpiece of the stethoscope is in proper contact with a body surface.

Solution to Problem

In order to solve the above problems, the present invention has the following configurations.

According to claim 1, a stethoscope includes a stethoscopic portion including a chestpiece, and a microphone provided in the chestpiece or in a hollow tube connected to the chestpiece; and a sensor for detecting contact with a human body when abutting on it, wherein the sensor is fixed to the chestpiece such that, in a state of detecting contact, an abutting end of the sensor is positioned at the same level as a contact surface of the chestpiece contacted with a human body or on a side slightly separated from a human body relative to the contact surface, whereby the sensor detects contact with a human body; wherein the abutting end of the sensor is movable in a contact direction relative to the chestpiece, energized by a resilient body to be positioned on a side slightly separated from a human body relative to the contact surface of the chestpiece contacted with a human body, and moved toward the contact surface when the chestpiece is pressed against a human body. Note that examples of the sensor include a sensor for detecting a variation in electrical resistance caused by a contact end contacted with a human body, a sensor for detecting pressure of contact of a contact end with a human body, a sensor for detecting the temperature of a human body with a contact end, a push switch turned on due to the pressing of a contact end caused by contact with a human body, and the like.

According to claim 2, in the stethoscope, the abutting end of the sensor is provided around the chestpiece.

According to claim 3, in the stethoscope according to claim 1, the chestpiece has a circular shape, the abutting ends of the sensor is provided at two positions, and a projection of a line segment connecting abutting ends projected onto a plane including the abutment surface is formed to pass through or near the center of the chestpiece.

According to claim 4, in the stethoscope, the abutting ends of the sensors are positioned on the side slightly away from the contact surface of the chestpiece contacted with a human body.

According to claim 5, in the stethoscope, the abutting end of the sensor is provided in a plurality, and a lamp that is lit when all of the abutting ends detect contact with a human body is provided on a side of the chestpiece opposite to the contact surface contacted with a human body.

According to claim 6, in the stethoscope according to claim 1, the abutting end of the sensor is provided in a plurality, and for each of the abutting ends, a lamp that is lit when the abutting end detects contact with a human body is provided on a side of the chestpiece opposite to the contact surface contacted with a human body.

According to claim 7, in the stethoscope, the sensors are electrodes for measuring electrocardiogram including at least a positive electrode and a negative electrode, and a surface of each of the electrodes contacted with a human body forms the abutting end.

Advantageous Effects of Invention

The present invention configured as described above will provide the following effects.

In the invention according to claim 1, in a case where the position of the abutting end is at the same level as the contact surface of the chestpiece contacted with the human body in a state of detecting contact, the contact with the human body is detected upon contact of the chestpiece with the human body. In addition, in a case where the position of the abutting end is on a side slightly away from a human body relative to the contact surface of the chestpiece contacted with a human body in a state of detecting contact, the contact with the human body is detected upon pressing of the chestpiece. Therefore, when the sensor detects contact with a human body, the chestpiece is also in contact with the human body. Thus, when the detection result of the sensor is presented by, for example, light, sound, notification through communication, or the like, a person placing the chestpiece on him/herself, a remote doctor, and the like can recognize the contact of the chestpiece of the stethoscope with the human body.

In the invention according to claim 2, the abutting end of the sensor is provided at three positions around the chestpiece. Thus, contact of the three abutting ends with a human body indicates surface-contact of the contact surface of the chestpiece with the human body, and it becomes possible to detect the contact of the chestpiece with the human body more properly.

In the invention according to claim 3, a projection of a line segment connecting the abutting ends passes through or near the center of the chestpiece. Thus, contact of the two abutting ends with a human body also indicates surface-contact of the circular contact surface of the chestpiece with the human body, and it is also possible to detect the contact of the chestpiece with the human body more properly.

In the invention according to claim 4, the abutting ends of the sensors are positioned on the side slightly away from the human body relative to the contact surface of the chestpiece contacted with a human body in a state of detecting contact.

Thus, the contact of the chestpiece with the human body is detected with the abutting ends of the sensor when the chestpiece is pressed against the human body, enabling more reliable detection of contact of the chestpiece with a human body.

In the invention according to claim 4, lighting of the lamp enables recognition that all of the plurality of abutting ends are contacted with a human body. Thus a person placing the chestpiece on him/herself can confirm proper contact of the chestpiece. Furthermore, a remote person looking at an image on a videophone or the like can recognize that the chestpiece is contacted with the human body. In addition, compared with a configuration for notifying contact through communication or the like, the invention can be formed to have a simpler structure, contributing to cost reduction.

In the invention according to claim 5, lightning of each of the lamps enables recognition that corresponding one of the plurality of abutting ends is contacted with a human body. Thus a remote person looking at an image on a videophone can recognize contact of the chestpiece with the human body when all of the lamps are lit. Moreover, the invention can be formed to have a simpler structure, contributing to cost reduction.

In the invention according to claim 6, the abutting ends of the sensors are contacted with the human body and detect the contact only when the chestpiece is brought into contact with a human body is further pressed against the human body. Thus, the contact of the chestpiece with the human body can be detected more reliably. At this time, deformation of the human body surface is not necessary. Especially, in a case where the abutting ends of the sensors detecting the contact with a human body are positioned at the same level as the contact surface of the chestpiece contacted with a human body, the sensors detect the contact with the human body only when a pressure is applied to the chestpiece. Thus, firm abutment of the chestpiece with the human body surface can be detected.

In the invention according to claim 7, the contact surface of the chestpiece is brought into abutment with a human body surface and the contact surfaces of the three electrodes constituting the electrodes for measuring electrocardiogram, serving also as the sensors, are simultaneously brought into contact with the human body. Thus, it is possible to simultaneously acquire a heart sound and an electric signal for electrocardiogram, which have been separately measured conventionally, by single operation.

DESCRIPTION OF EMBODIMENTS

Hereinafter, embodiments of the present invention will be described with reference to the drawings.

First Embodiment

Figure 1:
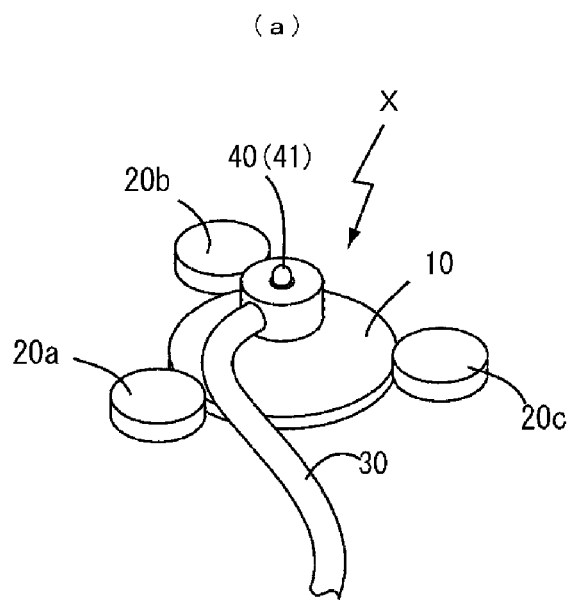
FIG. 1(a) is a perspective view of a front side of a stethoscope with electrodes for measuring electrocardiogram according to a first embodiment.
FIG. 1(b) is a perspective view of a back side of the stethoscope with electrodes for measuring electrocardiogram according to the first embodiment.
Figure 1:
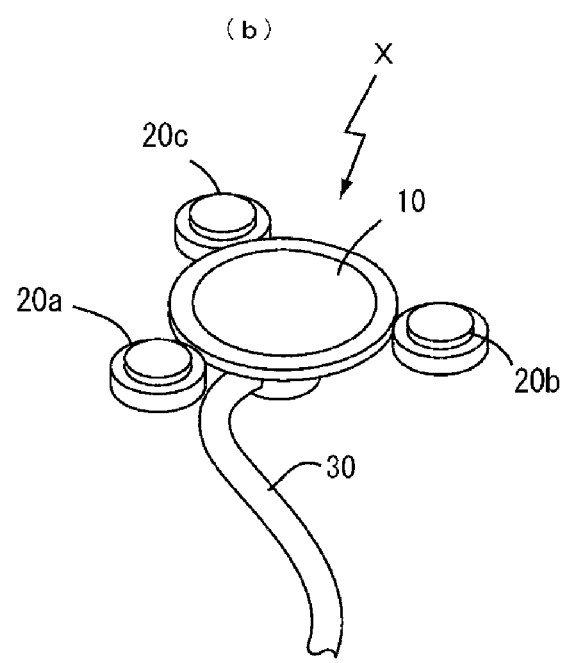

FIG. 1(a) illustrates a perspective view of a front side of a stethoscope X according to the present embodiment, and FIG. 1(b) illustrates a perspective view of a back surface of the stethoscope X. The stethoscope X includes a stethoscopic portion 10, sensors 20a, 20b, and 20c, an electric cable 30, and a notification unit 40. The stethoscopic portion 10 has almost the same structure as that of a chestpiece portion of a general diaphragm-type stethoscope, but has a built-in microphone for converting a sound into an electric signal. The sensors 20a, 20b, and 20c are constituted of push switches arranged around the stethoscopic portion 10 to form an equilateral triangle. A push switch constituting each of the sensors 20a, 20b, and 20c is arranged so that an end surface of a push button faces a body in medical examination, and the end surface of the push button constitutes a contact end contacted with the body. The contact ends are formed to be positioned on a side slightly away from a body relative to a diaphragm surface of the auscultation portion 10 when the contact ends are pressed by the body to which the contact ends are brought into contact and the switches are turned on. Note that while no force is applied to the contact ends, the contact ends may be located closer to the body than the diaphragm surface. The notification unit 40 includes an LED lamp 41 provided on the opposite side to the diaphragm surface of a chestpiece portion of the stethoscopic portion 10, and an electric circuit, not illustrated, provided inside the chestpiece portion to light the LED lamp 41 when all of the push switches constituting the sensors 20a, 20b, and 20c are turned on. An electric wire electrically connected to the notification unit 40 and an electric wire connected to the microphone built in the auscultation portion 10 are accommodated in the electric cable 30. A predetermined electrical connector is connected to base ends, not illustrated, of the electric wires located at a base end of the electric cable 30.

Figure 2:
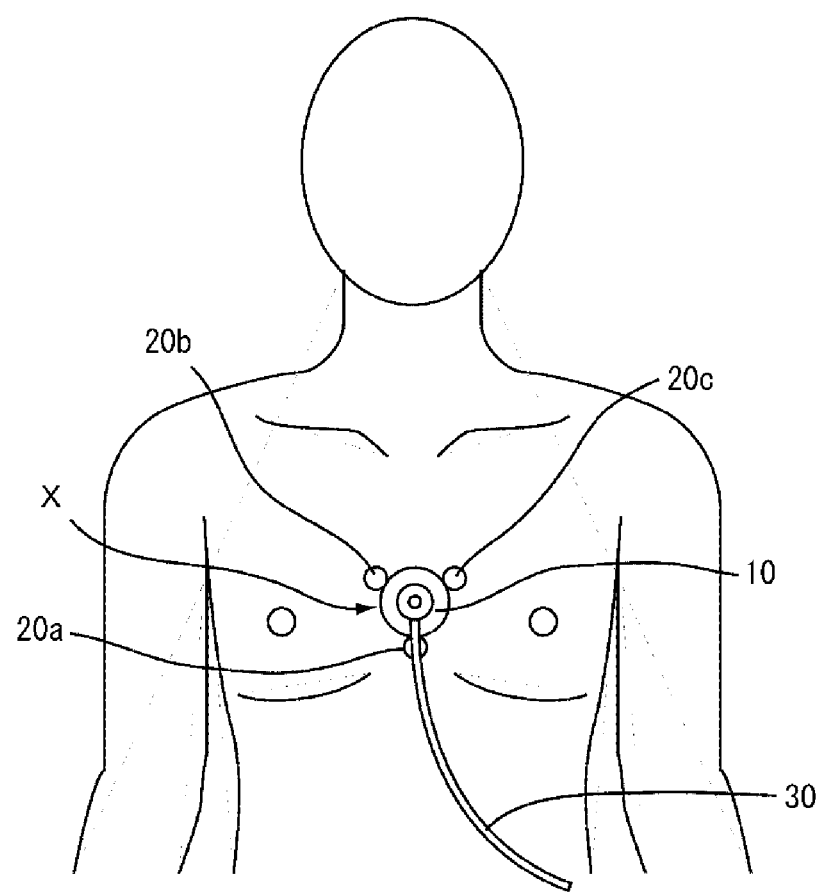
FIG. 2 is a diagram illustrating usage of the stethoscope with electrodes for measuring electrocardiogram according to the first embodiment.
Figure 3:
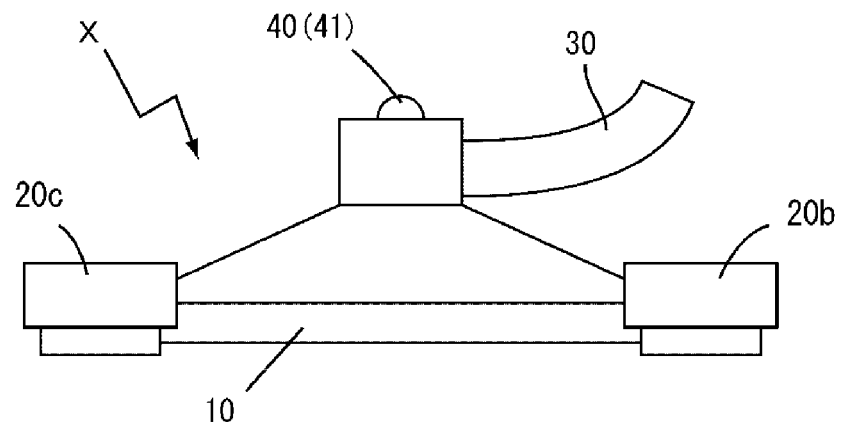
FIG. 3(a) is a side view of the stethoscope with electrodes for measuring electrocardiogram according to the first embodiment before being brought into contact with a body.
FIG. 3(b) is a side view of the stethoscope with electrodes for measuring electrocardiogram according to the first embodiment, being in contact with the body.
Figure 3:
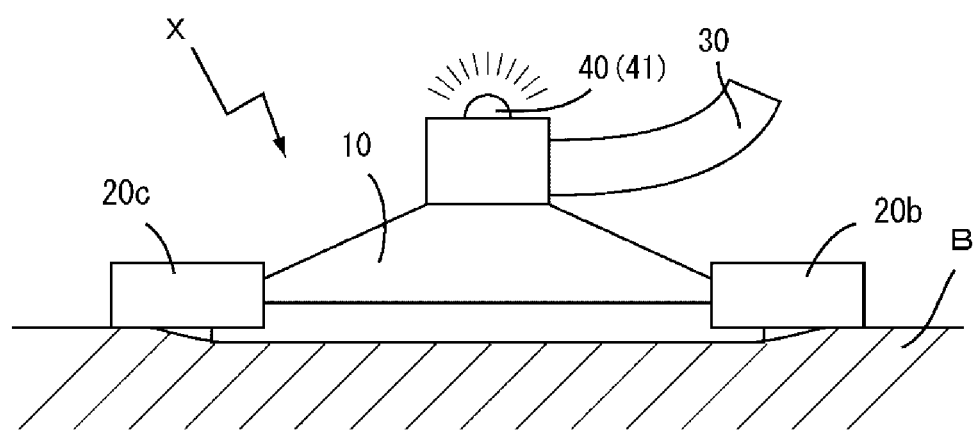

Next, a method of using the stethoscope X having the above configuration will be described. Here, a measuring person measures his/her own body by him/herself. First, the measuring person connects the electrical connector at the base end of the electric cable 30, not illustrated, to a videophone or the like. Thereafter, as illustrated in FIG. 2, the measuring person presses the diaphragm surface of the stethoscopic portion 10 against his/her body at an appropriate position near the heart. In the figures, although the measuring person's hand is not illustrated for ease of viewing the stethoscope X, actually, the stethoscope X is held by a hand of the measuring person and pressed. At this time, contact end surfaces of the push buttons of the sensors 20a, 20b, and 20c simultaneously abut on the body surface near the heart. FIG. 3(a) illustrates a side view of the stethoscope X immediately before being brought into contact with a body B, and FIG. 3(b) illustrates a side view of the stethoscope X in a state where the stethoscopic portion 10 is firmly brought into contact with the body B. When the diaphragm surface of the stethoscopic portion 10 is gently brought into contact with the body B from the state as illustrated in FIG. 3(a), the sensors 20a, 20b, and 20c are not switched on. When the diaphragm surface of the stethoscopic portion 10 is further pressed into abutment on the body B as illustrated in FIG. 3(b), the contact end surfaces of the button switches constituting the sensors 20a, 20b, and 20c are pressed in a direction away from the body relative to the diaphragm surface, and the sensors 20a, 20b, and 20c are then switched on. When the button switches constituting all of the three sensors 20a, 20b, and 20c are switched on, the LED lamp 41 of the notification unit 40 is lit. In this state, heart sound is converted into an electric signal by the microphone in the stethoscopic portion 10 and is transmitted to a remote doctor or the like through a videophone or the like connected to the stethoscope X. Then, lighting of the LED 41 allows the remote doctor or the like to recognize proper contact of the chestpiece of the stethoscope X with the body surface via the videophone or the like, enabling diagnosis of the heart sound obtained through the microphone in this state.

The stethoscope X according to the present embodiment enables visual recognition, from a remote position, of secured abutment of the diaphragm of the stethoscope X on a body owing to light emission of the LED lamp 41 by the operation described above.

Second Embodiment

Figure 4:
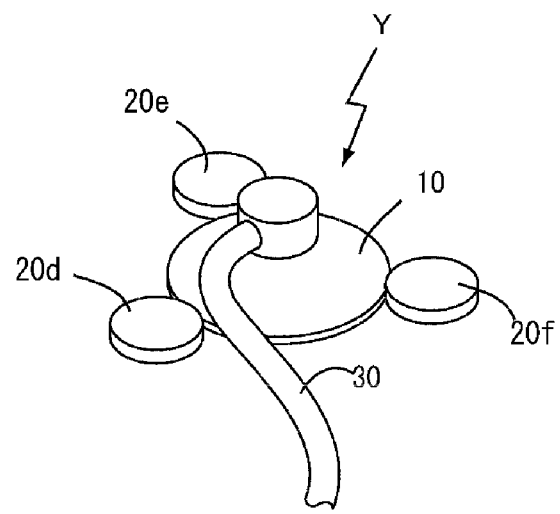
FIG. 4(a) is a perspective view of a front side of a stethoscope with electrodes for measuring electrocardiogram according to a second embodiment.
FIG. 4(b) is a perspective view of a back side of the stethoscope with electrodes for measuring electrocardiogram according to the embodiment.
Figure 4:
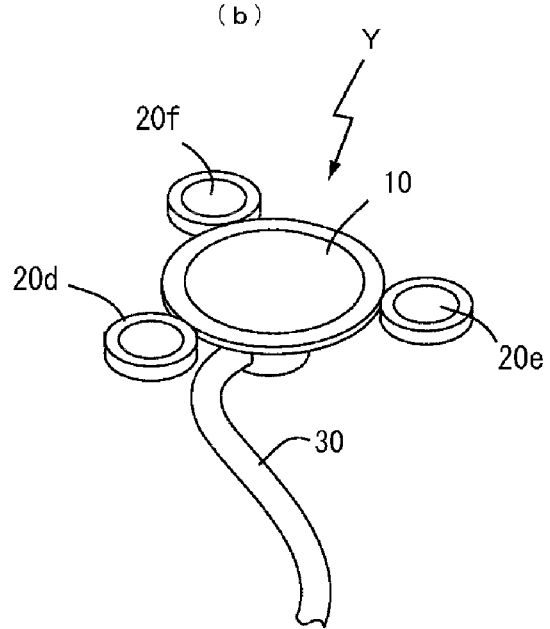

FIG. 4(a) illustrates a perspective view of a front side of a stethoscope Y with electrodes for measuring electrocardiogram according to a second embodiment, and FIG. 4(b) illustrates a perspective view of a back surface of the stethoscope Y. The stethoscope Y includes a stethoscopic portion 10, electrodes 20d, 20e, and 20f for measuring electrocardiogram, and an electric cable 30. The stethoscopic portion 10 has almost the same structure as that of a chestpiece portion of a general diaphragm-type stethoscope, but includes therein a microphone for converting a sound into an electric signal. The electrodes 20d, 20e, and 20f for measuring electrocardiogram are electrodes arranged around the stethoscopic portion 10 to form an equilateral triangle, and constitute a positive electrode, a negative electrode, and a ground electrode, respectively. Each of the electrodes 20d, 20e, and 20f for measuring electrocardiogram is fixed inside an elastomeric cover integrally fixed to the stethoscopic portion 10 on the back side, and the electrodes 20d, 20e, and 20f are formed such that exposed surfaces of the electrodes 20d, 20e, and 20f for electrocardiogram and a diaphragm surface of the auscultation portion 10 lie on substantially the same plane. Accordingly, when the diaphragm surface of the auscultation portion 10 is brought into contact with a body surface corresponding to a heart portion, the exposed surfaces of the electrodes 20d, 20e, and 20f for measuring electrocardiogram are also contacted with the body surface properly. An electrical wire connected to the electrodes 20d, 20e, and 20f for measuring electrocardiogram and an electric wire connected to the microphone built in the auscultation portion 10 are accommodated in the electric cable 30. A predetermined electrical connector is connected to base ends, not illustrated, of the electric wires located at a base end of the electric cable 30.

Next, a method of using the stethoscope Y having the above configuration will be described. First, a measuring person connects the electrical connector at the base end of the electric cable 30, not illustrated, to a measuring device or a communication device. Thereafter, similarly to the stethoscope X according to the first embodiment of FIG. 2, the stethoscopic portion 10 is pressed against an appropriate position on a surface over a breast bone near the heart of a measured person. When the stethoscopic portion 10 is pressed, the exposed surfaces of the electrodes 20d, 20e, and 20f for measuring electrocardiogram having the exposed surfaces on the same plane are also in proper contact with the surface over the breast bone near the heart at the same time. Note that when the electrodes 20d, 20e, and 20f for measuring electrocardiogram are brought into contact with a body, as illustrated in FIG. 2, a negative electrode is positioned at an upper right portion, a ground electrode at an upper left portion, and a positive electrode at a lower portion. In this state, the stethoscopic portion 10 obtains an electric signal obtained by converting a sound around the heart by the microphone built in the stethoscopic portion 10, and obtains an electric signal for obtaining an electrocardiogram from each of the electrodes 20d, 20e, and 20f for measuring electrocardiogram. These electric signals are sent to the measuring device or the communication device.

As described above, the stethoscope X with electrodes for measuring electrocardiogram according to the present embodiment can simultaneously obtain a sound signal of heart sound and an electric signal for electrocardiogram by single operation, and a burden on a measuring person or a measured person can be reduced. Reception of an electric signal for electrocardiogram enables recognition of secured abutment of the diaphragm of the stethoscope on a body. Thus, the electric signal can be received even from a distant position, and it becomes possible to know whether the diaphragm of the stethoscope is in secured contact with the body.

Figure 5:
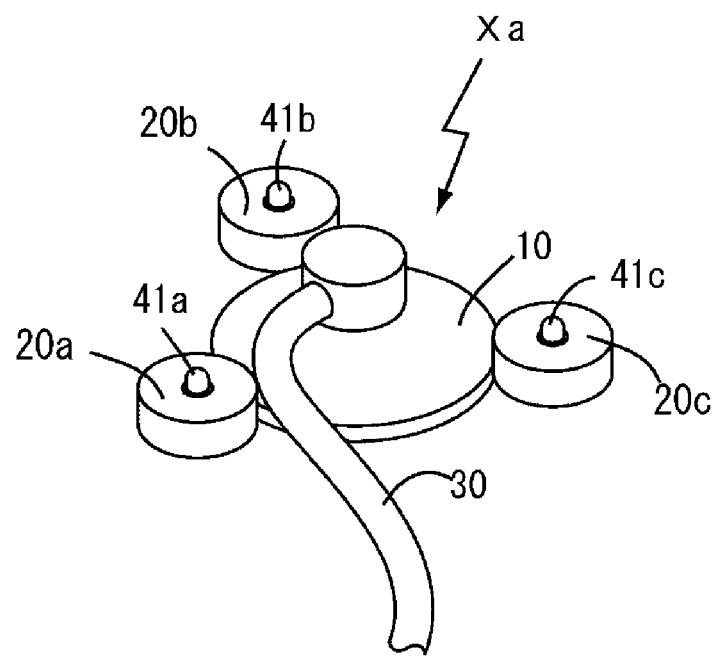
FIG. 5 is a perspective view of a front side of a stethoscope with electrodes for measuring electrocardiogram according to a first modification.

Note that in the first embodiment, the stethoscope X is formed to light the LED lamp 41 when the contact of all of the sensors 20a, 20b, and 20c with a body is detected. However, as in the stethoscope Xa illustrated in FIG. 5, LED lamps 41a, 41b, and 41c emitting light when contact with a body is detected may be provided on the sensors 20a, 20b, and 20c, respectively. In this configuration, secured contact of the diaphragm surface with a body should be determined on the basis of lighting of all of the three LED lamps 41a, 41b, and 41c.

Figure 6:
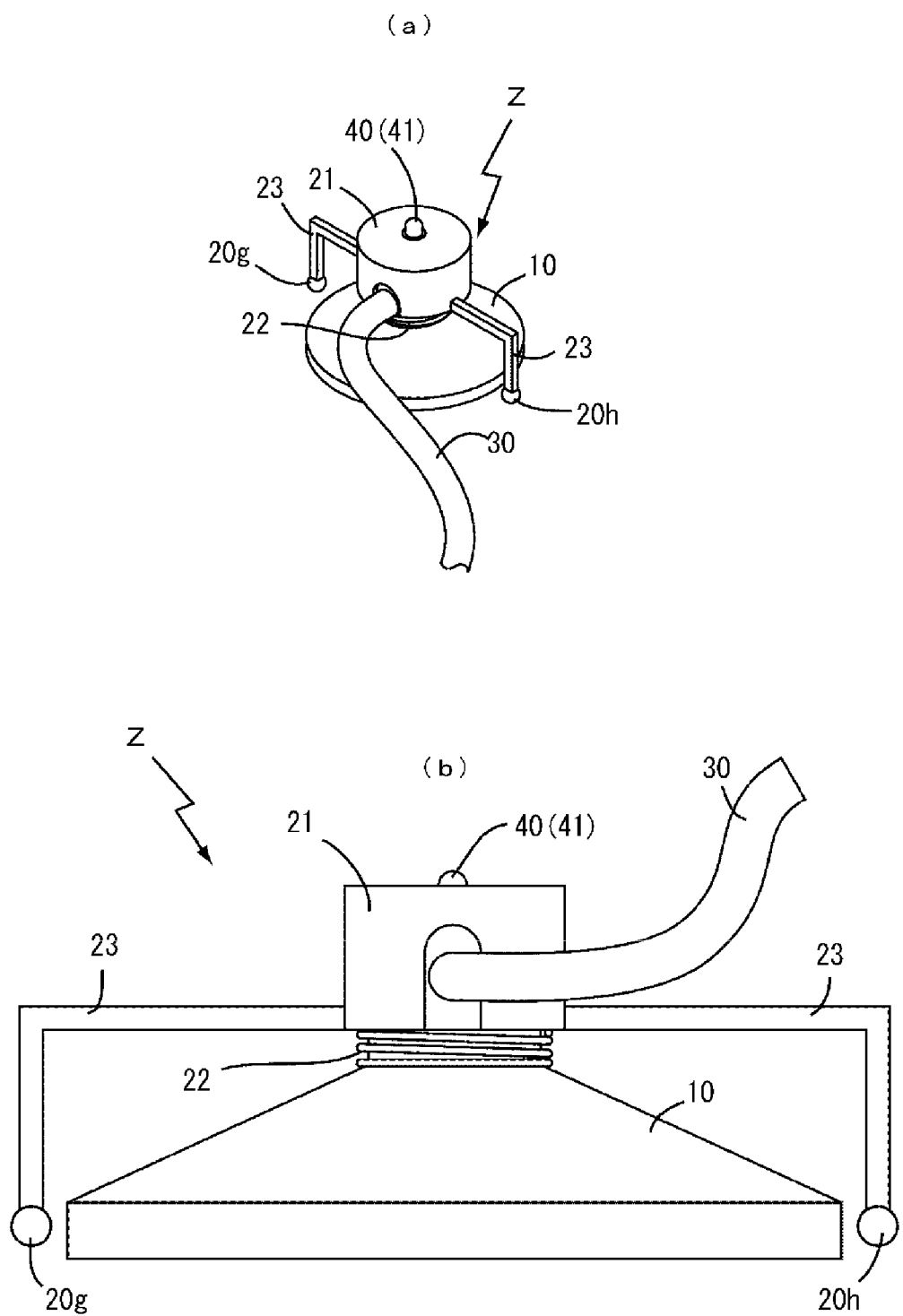
FIG. 6(a) is a perspective view of a front side of a stethoscope with electrodes for measuring electrocardiogram according to a second modification.
FIG. 6(b) is a side view of the stethoscope with electrodes for measuring electrocardiogram according to the second modification.

In the above embodiments, the positions of the contact ends of the sensors detecting contact with a human body is fixed to the chestpiece, but the positions of the contact ends may be relatively movable in the contact direction of the chestpiece. FIG. 6(a) illustrates a perspective view of a stethoscope Z as an example of a stethoscope having such a structure, and FIG. 6(b) illustrates a side view thereof. In the stethoscope Z, a cylindrical cap 21 is fixed to a cylindrical protruding portion having a built-in microphone on a side opposite to a diaphragm surface such that the cylindrical cap 21 is movable in a direction perpendicular to a chestpiece surface. The cap 21 is formed not to come off upward in FIGS. 6(a) and 6(b) by a retaining structure, not illustrated, a compression spring 22 is provided between a lower side of the cap 21 and the side opposite to the diaphragm surface, and the compression spring 22 energizes the cap 21 in a direction away from the diaphragm surface. Note that an LED lamp 41 of a notification unit 40 is provided on an upper surface of the cap 21 in the figures. The sensors 20g and 20h are electrodes having spherical contact ends, and the LED 41 is lit when both electrodes contacted with the body. The sensors 20*g* and 20*h* are fixed to the cap 21 via arms 23 and 23. The stethoscope Z is formed such that the contact ends of the sensors 20*g* and 20*h* are located on a side away from the body relative to the diaphragm surface by compression of the compression spring 22 in a state where no force is applied while the contact ends are formed to project to the body relative to the diaphragm surface when the compression spring is contracted by pressing the cap 21 toward the diaphragm surface side.

Due to this structure, the stethoscope Z is in a state where the contact ends of the sensors 20*g* and 20*h* are apart from the body when the diaphragm surface is in gentle contact with a body, and thus the sensors 20*g* and 20*h* do not detect contact with the body. On the other hand, when the diaphragm surface is brought into contact with the body and then the cap 21 is further pressed toward the body side to contract the compression spring 22 under the pressure, the contact ends of the sensors 20*g* and 20*h* are brought into contact with the body, and thus the sensors 20*g* and 20*h* detect the contact with the body. That is, when the contact ends of the sensors are positioned away from a body relative to the diaphragm surface, the contact ends of the sensors can be brought into contact with a body without pressing the diaphragm surface against the body. Therefore, even when the body surface cannot be easily deformed, it can be recognized that the diaphragm surface is in contact with the body with sufficient contact pressure.

Furthermore, in the first and second embodiments, three contact ends of the sensors are provided. This is because the three contact points form a plane and thus enable recognition that the whole of the diaphragm surface is in contact with a body. However, since the diaphragm surface has a certain size, two contact ends of the sensors may be provided as in the stethoscope Z illustrated in FIGS. 6(*a*) and 6(*b*). In this configuration, when a line segment connecting the contact points of the two contact ends to a body is projected onto a plane including the diaphragm surface, the contact ends should be formed such that the projected line segment passes through a chord of the circular diaphragm surface, and preferably passes through or near the center of the circle. With this configuration, when the contact ends of the sensors are positioned at the same level as the diaphragm surface or away from a human body relative to the diaphragm surface, both contact ends of the sensors are hardly contacted with the body with the diaphragm surface in point-contact with the body. Therefore, it is practically possible to recognize surface-contact of the diaphragm surface with the body on the basis of the contact of the two contact ends of the sensors with the body.

In the above embodiments, the microphone of the stethoscopic portion 10 is built in the chestpiece, but a hollow tube may be provided though the electric cable 30 to transmit sound from the chestpiece, and the microphone may be provided in the hollow tube or at a base end of the hollow tube.

In the second embodiment, the contact end surfaces of the electrodes 20*d*, 20*e*, and 20*f* for measuring electrocardiogram may be arranged slightly retracted from the diaphragm surface of the chestpiece so that the electrodes 20*d*, 20*e*, and 20*f* for measuring electrocardiogram are not contacted with a body until the chestpiece is pressed against the body to allow recognition of secured contact of the diaphragm surface with the human body similarly to the first embodiment. In contrast, the exposed surfaces of the electrodes 20*a*, 20*b*, and 20 for measuring electrocardiogram may be slightly protruded from the diaphragm surface of the chestpiece. With this configuration, when the chestpiece of the stethoscopic portion 10 is placed on a human body, the electrodes 20*a*, 20*b*, and 20*c* for measuring the electrocardiogram are pressed against the human body, and firm contact of the electrodes 20*a*, 20*b*, and 20*c* for measuring electrocardiogram with the human body can be achieved.

Furthermore, in the second embodiment, the electrodes 20*a*, 20*b*, 20*c* for measuring electrocardiogram are arranged to form an equilateral triangle, but the electrodes may be arranged to form an isosceles triangle or the like, and depending on the application, two unipolar leads may be used, as long as electrocardiogram information that is sufficient to detect systole can be obtained.

Still further, in addition to the push switch described in the first embodiment and the electrodes described in the second embodiment, various sensors that can detect the contact with a body, such as a pressure sensor and a temperature sensor, may be used as sensors to be made contact with the body.

In addition, as means for notifying contact of the sensors with a body, various methods that allows a person placing the chestpiece on him/herself to recognize contact of the chestpiece and allows recognition of the contact from a remote place can be used in addition to lighting of the LED lamp described in the first embodiment, and reception of an electric signal described in the second embodiment. Various methods include a method for notifying using sound such as a buzzer, and a method for displaying text data or the like on a monitor,

REFERENCE SIGNS LIST

X, Y, Xa, Z STETHOSCOPE
10 STETHOSCOPIC PORTION
20*a*, 20*b*, 20*c*, 20*d*, 20*e*, 20*f*, 20*g*, 20*h* SENSOR
30 ELECTRICAL CABLE
40 NOTIFICATION UNIT
41 LED LAMP

The invention claimed is:

1. A stethoscope comprising:
    a stethoscopic portion including a chestpiece, and a microphone provided in the chestpiece or in a hollow tube connected to the chestpiece; and
    a sensor for detecting contact with a human body when abutting on it, wherein the sensor is fixed to the chestpiece such that, in a state of detecting contact, an abutting end of the sensor is positioned at the same level as a contact surface of the chestpiece contacted with a human body or on a side slightly separated from a human body relative to the contact surface, whereby the sensor detects contact with a human body;
    wherein the abutting end of the sensor is movable in a contact direction relative to the chestpiece, energized by a resilient body to be positioned on a side slightly separated from a human body relative to the contact surface of the chestpiece contacted with a human body, and moved toward the contact surface side when the chestpiece is pressed against a human body.

2. The stethoscope according to claim 1, wherein
    the abutting end of the sensor is provided at three positions around the chestpiece.

3. The stethoscope according to claim 1, wherein
    the contact surface of the chestpiece has a circular shape, the abutting end of the sensor is provided at two positions, and a projection of a line segment connecting the abutting ends projected onto a plane including the abutment surface is formed to pass through or near the center of the chestpiece.

4. The stethoscope according to claim 1, wherein
the abutting ends of the sensors are positioned on the side slightly separated from the contact surface of the chestpiece contacted with a human body.

5. The stethoscope according to claim 1, wherein
the abutting end of the sensor is provided in a plurality, and a lamp that is lit when all of the abutting ends detect contact with a human body is provided on a side of the chestpiece opposite to the contact surface contacted with a human body.

6. The stethoscope according to claim 1, wherein
the abutting end of the sensor is provided in a plurality, and a lamp that is lit when the abutting end detects contact with a human body is provided, for each of the abutting ends, on a side of the chestpiece opposite to the contact surface contacted with a human body.

7. The stethoscope according to claim 1, wherein
the sensors are electrodes for measuring electrocardiogram including at least a positive electrode and a negative electrode, and a surface of each of the electrodes contacted with a human body forms the abutting end.

* * * * *